(12) United States Patent
Ren et al.

(10) Patent No.: US 7,419,728 B2
(45) Date of Patent: Sep. 2, 2008

(54) LIGHT-EMITTING DEVICE CONTAINING BIS-PHOSPHINEOXIDE COMPOUND

(75) Inventors: Xiaofan Ren, Rochester, NY (US); David J. Giesen, Webster, NY (US)

(73) Assignee: Eastman Kodak Company, Rochester, NY (US)

( * ) Notice: Subject to any disclaimer, the term of this patent is extended or adjusted under 35 U.S.C. 154(b) by 309 days.

(21) Appl. No.: 11/141,092

(22) Filed: May 31, 2005

(65) Prior Publication Data

US 2006/0269784 A1    Nov. 30, 2006

(51) Int. Cl.
*H01L 51/54* (2006.01)
(52) U.S. Cl. .................. 428/690; 313/504; 313/506; 428/917; 257/40
(58) Field of Classification Search .......... 428/690, 428/917; 313/504, 506; 257/40, E51.026
See application file for complete search history.

(56) References Cited

U.S. PATENT DOCUMENTS

2004/0046495 A1* 3/2004 Peng ................ 313/504

2005/0106413 A1    5/2005 Tanaka et al.

FOREIGN PATENT DOCUMENTS

| EP | 1 378 532 | 1/2004 |
| JP | 2002-63989 | 2/2002 |
| JP | 2003/317965 | 11/2003 |
| JP | 2004-95221 | 3/2004 |
| JP | 2004/204140 | 7/2004 |
| WO | WO 2005003253 A2 * | 1/2005 |
| WO | 2005/073340 | 8/2005 |
| WO | 2005/104628 | 11/2005 |

OTHER PUBLICATIONS

P. E. Burrows, et al., "Ultraviolet electroluminescence and blue-green phosphorescence using an organic diphosphine oxide charge transporting layer", Applied Physics Letters, 88, 2006.
I. Avilov, et al., "Quantum-chemical Design of Host Materials for Full-Color Triplet Emission", Advanced Materials, 16, No. 18, Sep. 16, 2004, pp. 1624-1629.

* cited by examiner

*Primary Examiner*—Dawn Garrett
(74) *Attorney, Agent, or Firm*—Arthur E. Kluegel

(57) ABSTRACT

An OLED device comprises an anode and a cathode and having therebetween a light emitting layer containing an emissive material, wherein a layer between the anode and cathode contains a phosphineoxide compound bearing two or more tri(hetero)arylphosphineoxide groups, provided these groups are selected to give a compound with a $E_t \geq 2.65$ eV.

13 Claims, 1 Drawing Sheet

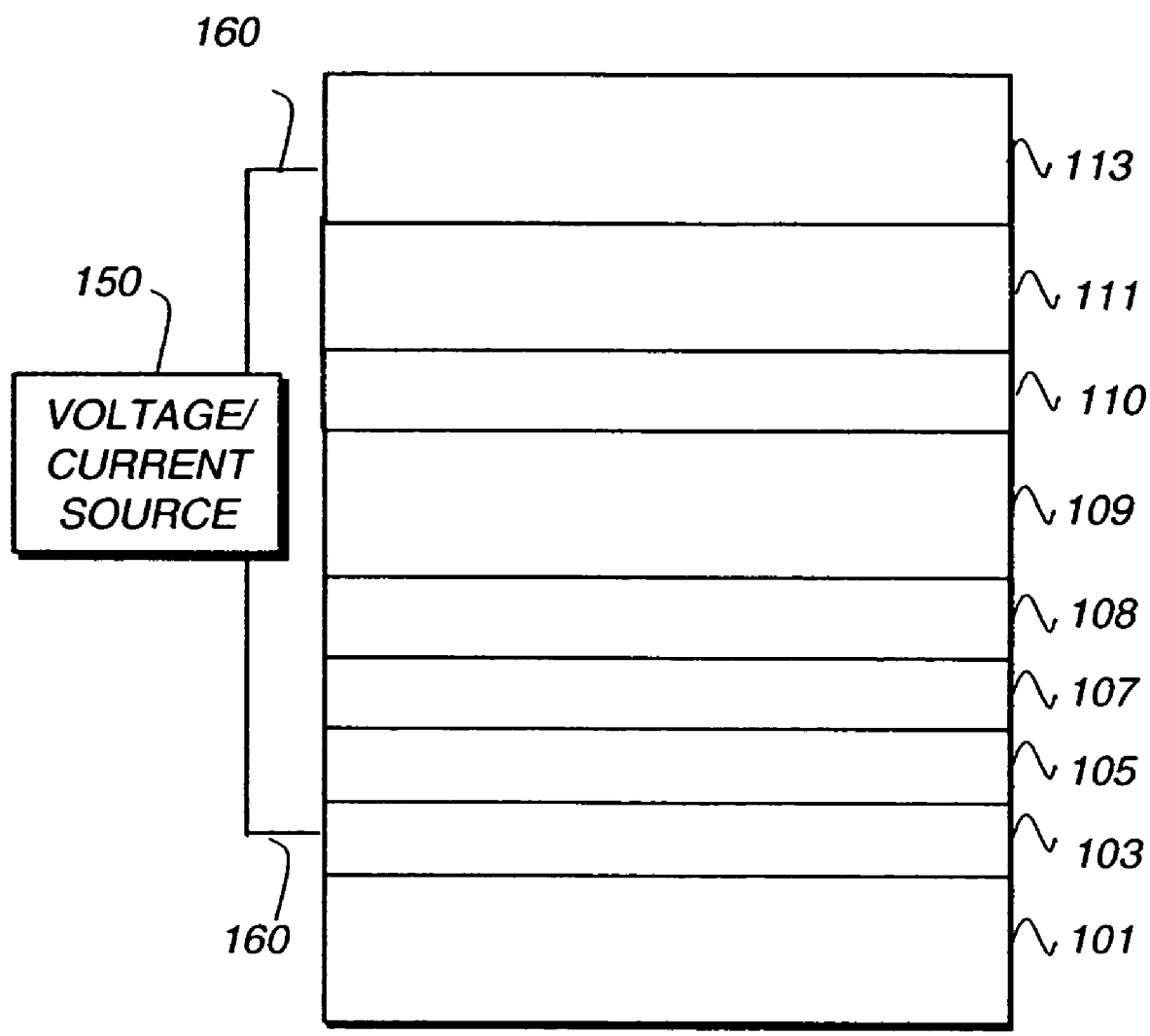

US 7,419,728 B2

LIGHT-EMITTING DEVICE CONTAINING BIS-PHOSPHINEOXIDE COMPOUND

FIELD OF INVENTION

This invention relates to organic electroluminescent (EL) devices containing a bis-phosphineoxide compound.

BACKGROUND OF THE INVENTION

While organic electroluminescent (EL) devices have been known for over two decades, their performance limitations have represented a barrier to many desirable applications. In simplest form, an organic EL device is comprised of an anode for hole injection, a cathode for electron injection, and an organic medium sandwiched between these electrodes to support charge recombination that yields emission of light. These devices are also commonly referred to as organic light-emitting diodes, or OLEDs. Representative of earlier organic EL devices are Gurnee et al. U.S. Pat. No. 3,172,862, issued Mar. 9, 1965; Gurnee U.S. Pat. No. 3,173,050, issued Mar. 9, 1965; Dresner, "Double Injection Electroluminescence in Anthracene", RCA Review, Vol. 30, pp. 322-334, 1969; and Dresner U.S. Pat. No. 3,710,167, issued Jan. 9, 1973. The organic layers in these devices, usually composed of a polycyclic aromatic hydrocarbon, were very thick (much greater than 1 μm). Consequently, operating voltages were very high, often >100V.

More recent organic EL devices include an organic EL element consisting of extremely thin layers (e.g. <1.0 μm) between the anode and the cathode. Herein, the term "organic EL element" encompasses the layers between the anode and cathode electrodes. Reducing the thickness lowered the resistance of the organic layer and has enabled devices that operate much lower voltage. In a basic two-layer EL device structure, described first in U.S. Pat. No. 4,356,429, one organic layer of the EL element adjacent to the anode is specifically chosen to transport holes, therefore, it is referred to as the hole-transporting layer, and the other organic layer is specifically chosen to transport electrons, referred to as the electron-transporting layer. Recombination of the injected holes and electrons within the organic EL element results in efficient electroluminescence.

There have also been proposed three-layer organic EL devices that contain an organic light-emitting layer (LEL) between the hole-transporting layer and electron-transporting layer, such as that disclosed by Tang et al [*J. Applied Physics*, Vol. 65, Pages 3610-3616, 1989]. The light-emitting layer commonly consists of a host material doped with a guest material. Still further, there has been proposed in U.S. Pat. No. 4,769,292 a four-layer EL element comprising a hole-injecting layer (HIL), a hole-transporting layer (HTL), a light-emitting layer (LEL) and an electron transport/injection layer (ETL). These structures have resulted in improved device efficiency.

In organic electroluminescent devices, only 25% of electrons and holes recombine as singlet states while 75% recombine as triplet states according to simple spin statistics. Singlet and triplet states, and fluorescence, phosphorescence, and intersystem crossing are discussed in J. G. Calvert and J. N. Pitts, Jr., *Photochemistry* (Wiley, New York, 1966). Emission from triplet states is generally very weak for most organic compounds because the transition from triplet excited state to singlet ground state is spin-forbidden. Hence, many emitting materials that have been described as useful in an OLED device emit light from their excited singlet state by fluorescence and thereby utilize only 25% of the electron and hole recombinations. However, it is possible for compounds with states possessing a strong spin-orbit coupling interaction to emit strongly from triplet excited states to the singlet ground state (phosphorescence). One such strongly phosphorescent compound is fac-tris(2-phenyl-pyridinato-N^C-)Iridium(III) (Ir(ppy)$_3$) that emits green light (K. A. King, P. J. Spellane, and R. J. Watts, *J. Am. Chem. Soc.*, 107, 1431 (1985), M. G. Colombo, T. C. Brunold, T. Reidener, H. U. Güdel, M. Fortsch, and H. -B. Bürgi, *Inorg. Chem.*, 33, 545 (1994)). Organic electroluminescent devices having high efficiency have been demonstrated with Ir(ppy)$_3$ as the phosphorescent material and 4,4'-N,N'-dicarbazole-biphenyl (CBP) as the host (M. A. Baldo, S. Lamansky, P. E. Burrows, M. E. Thompson, S. R. Forrest, *Appl. Phys. Lett.*, 75, 4 (1999), T. Tsutsui, M. -J. Yang, M. Yahiro, K. Nakamura, T. Watanabe, T. Tsuji, Y. Fukuda, T. Wakimoto, S. Miyaguchi, *Jpn. J. Appl. Phys.*, 38, L1502 (1999)). Additional disclosures of phosphorescent materials and organic electroluminescent devices employing these materials are found in U.S. Pat. No. 6,303,238 B1, WO 00/57676, WO 00/70655 and WO 01/41512 A1.

Few organic-based emissive materials can be deposited as neat films. Usually it is necessary to codeposit them with a host material, either a charge transporting "small" molecule or a polymer, to get a reasonable light output. Well known host materials for dopant-host system include hole transporting 4,4'-N,N'-dicarbazole-biphenyl (CBP) and electron transporting aluminum tris(8-hydroxylquinoline) (Alq), which have been both used in OLEDs. However, the known host materials are not suitable host materials for all dopants. There continues to be a need in the art for suitable host materials for dopants which have short emission wavelength, such as in the green or blue regions of the spectrum.

In the emissive layer of phosphorescent OLEDs, the host is generally selected to have a triplet energy higher than that of the phosphorescent dopant in order to avoid exothermic energy quenching to the host. In addition, it is desirable for the host material to be an efficient charge carrier to achieve low drive voltage of the devices (*Appl. Phys. Lett.*, 77, 904 (2000)). Host materials containing phosphineoxide have been disclosed in JP2003317965A and JP2004204140A. In both patent applications, the phosphineoxide group was used mainly as a linking group incorporating conventional charge (hole and electron) transporting units into one structure. The charge transporting ability of phosphineoxide itself has not been explored. Furthermore, the majority of the structures disclosed therein have triplet energies corresponding to emission in the red or deep red of the visible spectra. Publication JP2004204140A specifically requires that at least one naphthyl group be attached to the phosphorus atom (the triplet energy of naphthalene itself is 2.6 eV) consequently the triplet energy of the compounds should be no more than 2.6 eV. Therefore, there is a particular need in the art for host materials which can support dopants with green and blue phosphorescent emission.

It is a problem to be solved to provide a device containing a phosphorescent material in a light emitting layer, the device also containing a compound that enables high luminescent efficiency and low drive voltage.

SUMMARY OF THE INVENTION

The invention provides an OLED device comprising an anode and a cathode and having therebetween a light emitting layer containing an emissive material, wherein a layer between the anode and cathode contains a phosphineoxide compound bearing two or more tri(hetero)arylphosphineoxide groups, provided these groups are selected to give a compound with a Et≧2.65 eV.

Devices of the invention provide high luminescent efficiency and low drive voltage

BRIEF DESCRIPTION OF THE DRAWINGS

The FIGURE shows a schematic cross-section of a typical OLED device in which this invention may be used.

DETAILED DESCRIPTION OF THE INVENTION

As understood herein, a dopant and host system is one in which an emitter compound is doped into a host compound matrix. Overall, it is desired to obtain an emission from the dopant and host system such that the emission has a high intensity and is in the appropriate blue, green or red region of the visible spectrum.

Efficient energy transfer from the host to the dopant is preferred in order to prevent the emission of the host from interfering with the emission of the dopant, and to minimize the non-light-producing transitions in the system.

In a singlet dopant and host system, efficient energy transfer occurs when there is overlap between the emission spectrum of the host and the absorption spectrum of the dopant. However, where the host has a singlet-based emission spectrum, and the dopant has a triplet-based spectrum, this approximation does not hold. If the excited triplet state (T1) of the dopant is higher than that of the host, energy quenching to the host will occur and thus leads to non-light-producing transitions. In these circumstances, it is ordinarily preferable to select a host having a higher T1 state than the T1 state of the dopant to ensure efficient energy transfer. This becomes more difficult to achieve as the emission wavelength of the dopant becomes shorter, and the T1 state gets higher. One aspect of the invention lies in identifying suitable host materials by their T1 energy levels (actual or computed), relative to the T1 energy levels of the dopant.

In an embodiment of the invention, one or more layers between an anode and a cathode in an OLED device contains a phosphineoxide compound bearing two or more tri(hetero) arylphosphineoxide groups provided the tri(hetero) arylphosphineoxide groups are selected to give a compound with a triplet energy (Et)≧2.65 eV. It is particularly preferred for the compound to serve as a host material and form a major proportion of the light emitting layer. The proportion of the compound in the light-emitting layer is preferably 50 to 99.9% by weight, more preferably 80 to 99% by weight.

Where a compound functions as a host material, there is possibility that the compound may function as a charge carrier and be electrochemically oxidized or reduced in performing its function. Accordingly, it is desirable that the compound be stable against electrochemical oxidation or reduction. That is, the compound is preferably such that the oxidized species (e.g. radical cation species) or the reduced species (e.g. radical anion species) is stable.

Excitons of the host material are generated by hole/electron recombination in a host material. Therefore, it is preferable that the excited state of the host material be stable enough against decomposition or thermal deactivation. This means the host material should be stable to light too.

Thermal destruction of the film or thermal decomposition of the materials is a great cause of deterioration of an OLED, so it is preferred that the host material be capable of retaining a stable amorphous film form without undergoing thermal decomposition and crystallization even at high temperatures.

As described above, it is desirable for the compound used as a host material to be extremely stable against light, heat, and electrochemical oxidation/reduction. The OLED containing such a host compound is expected to exhibit markedly improved durability.

Due to the phosphineoxide moiety itself having electron transporting ability, the phosphineoxide compounds consisting of two or more phosphineoxide moieties are good electron transporters. The present inventors have found that they can function as excellent electron transporting materials and exciton/hole blocking materials in OLEDs.

In a preferred embodiment, the phosphineoxide compound is represented by the formula:

$(A)_nB$ wherein A is represented by

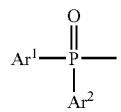

$n \geq 2$;

wherein $Ar^1$, $Ar^2$ and B each exhibit an Et≧2.65 eV.

$Ar^1$, $Ar^2$ and B are each an aromatic group or heteroaromatic group independently selected from phenyl, biphenyl, and heteroaryl with Et≧2.65 eV;

each of $Ar^1$, $Ar^2$ and B may be independently substituted with one or more of alkyl, alkenyl, alkoxy, aryl, aralkyl, halogen, $NH_2$, NHR, $NR_2$, $NO_2$ and CN;

and additionally or alternatively, one or more of $Ar^1$, $Ar^2$ and B may be linked together by a linking group selected from a covalent bond, —O—, —$CH_2$—, —CHR—, —$CR_2$—, —NH—, —NR—;

each R is selected from alkyl, alkenyl, aryl, and aralkyl; and

B is a (hetero)aromatic group with n bonds

In a further embodiment, the phosphine oxide compound is represented by the formula, wherein $Ar^1$ and $Ar^2$ is each phenyl group:

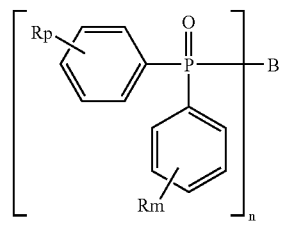

B is an aromatic group or heteroaromatic group independently selected from phenyl, biphenyl, and heteroaryl with Et≧2.65 eV;

each R is independently selected from alkyl, alkenyl, alkoxy, aryl, aralkyl, halogen, $NH_2$, NHR, $NR_2$, $NO_2$ and CN;

each of p and m is independently selected from the values 0, 1, 2, 3, 4 and 5; and n is equal or larger than 2.

Unless otherwise specifically stated, use of the term "substituted" or "substituent" means any group or atom other than hydrogen. Unless otherwise specifically stated, use of the term "aromatic ring system" means a system of one ring or more than one ring fused together, where the entire ring system is aromatic. Unless otherwise specifically stated, use of the term "substituted phenyl ring" means a phenyl ring that is substituted and may be substituted to form one substituted or unsubstituted fused aromatic ring system, or more than one substituted or unsubstituted fused aromatic ring systems. Unless otherwise provided, when a group (including a compound or complex) containing a substitutable hydrogen is referred to, it is also intended to encompass not only the unsubstituted form, but also form further substituted with any substituent group, or groups as herein mentioned, including a fused ring, so long as the substituent does not destroy properties necessary for utility. Suitably, a substituent group may be halogen or may be bonded to the remainder of the molecule by an atom of carbon, silicon, oxygen, or phosphorous.

If desired, the substituents may themselves be further substituted one or more times with the described substituent groups. The particular substituents used may be selected by those skilled in the art to attain the desired desirable properties for a specific application and can include, for example, electron-withdrawing groups, electron-donating groups, and steric groups.

The term "halo" or "halogen" as used herein includes fluorine, chlorine, bromine and iodine.

The term "alkyl" as used herein contemplates both straight and branched chain alkyl radicals. Preferred alkyl groups are those containing from one to fifteen carbon atoms and includes methyl, ethyl, propyl, isopropyl, butyl, isobutyl, tert-butyl, and the like. Additionally, the alkyl group may be optionally substituted with one or more substituents selected from halo, CN, $CO_2R$, C(O)R, $NR_2$, cyclic-amino, $NO_2$, and OR.

The term "cycloalkyl" as used herein comtemplates cyclic alkyl radicals. Preferred cycloalkyl groups are those containing 3 to 7 carbon atoms and includes cyclopropyl, cyclopentyl, cyclohexyl, and the like. Additionally, the cycloalkyl group may be optionally substituted with one or more substituents selected from halo, CN, $CO_2R$, C(O)R, $NR_2$, cyclic-amino, $NO_2$, and OR.

The term "alkenyl" as used herein contemplates both straight and branched chain alkene radicals. Preferred alkenyl groups are those containing two to fifteen carbon atoms. Additionally, the alkenyl group may be optionally substituted with one or more substituents selected from halo, CN, $CO_2R$, C(O)R, $NR_2$, cyclic-amino, $NO_2$, and OR.

The term "alkynyl" as used herein contemplates both straight and branched chain alkyne radicals. Preferred alkynyl groups are those containing two to fifteen carbon atoms. Additionally, the alkenyl group may be optionally substituted with one or more substituents selected from halo, CN, $CO_2R$, C(O)R, $NR_2$, cyclic-amino, $NO_2$, and OR.

The term "aralkyl" as used herein contemplates an alkyl group which has as a substituent an aromatic group. Additionally, the aralkyl group may be optionally substituted with one or more substituents selected from halo, CN, $CO_2R$, C(O)R, $NR_2$, cyclic-amino, $NO_2$, and OR.

The term "heteroaryl group" as used herein contemplates cyclic aromatic radicals that contain at least one heteroatom (for example, N, O, S, etc.) as one of the ring atoms. Heteroaryl groups can contain 5 or 6 ring atoms, which includes at least one heteroatom, for example, pyrrole, furan, thiophene, imidazole, thiazole, triazole, pyrazole, pyridine and pyrimidine, and the like. Additionally, the heteroaryl group may be optionally substituted with one or more alkyl, alkenyl, alkoxy, aryl, aralkyl, halogen, $NH_2$, NHR, $NR_2$, $NO_2$ and CN.

The term "aryl" or "aromatic group" as used herein contemplates aromatic groups, including substituted or unsubstituted phenyl, biphenyl and aromatic heterocyclic group such as substituted or unsubstituted pyridine, pyrimidine and the like. Additionally, the aromatic group may be optionally substituted with one or more alkyl, alkenyl, alkoxy, aryl, aralkyl, halogen, $NH_2$, NHR, $NR_2$, $NO_2$ and CN.

It is understood that the various embodiments described herein are by way of example only, and are not intended to limit the scope of the invention.

Useful compounds of this invention include:

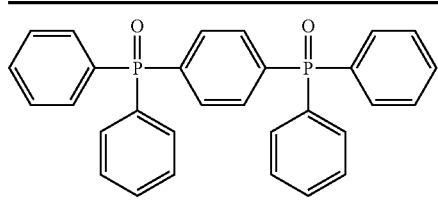

HM-1

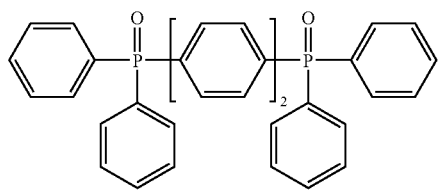

HM-2

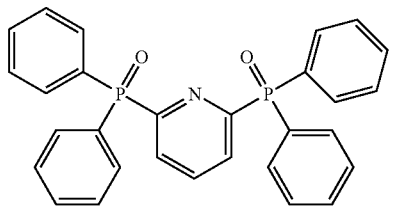

HM-3

-continued
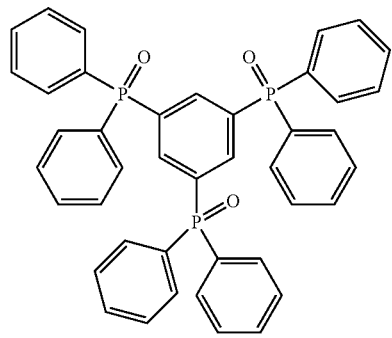
HM-4
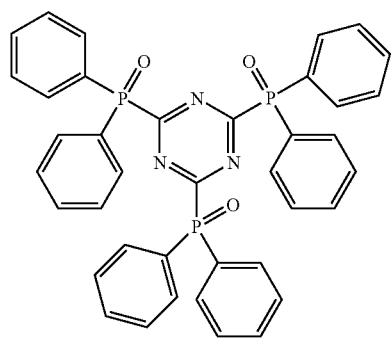
HM-5
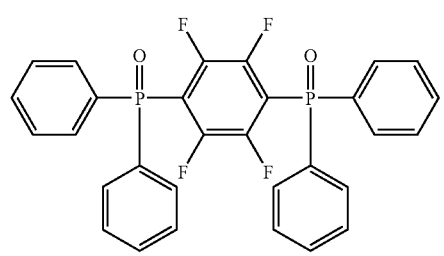
HM-6
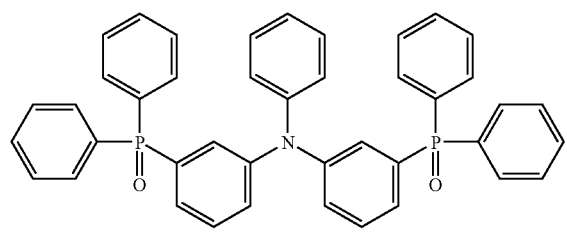
HM-7
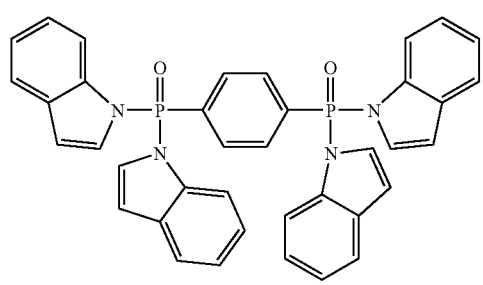
HM-8

-continued
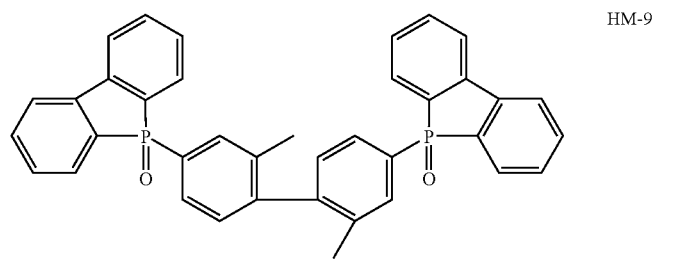
HM-9
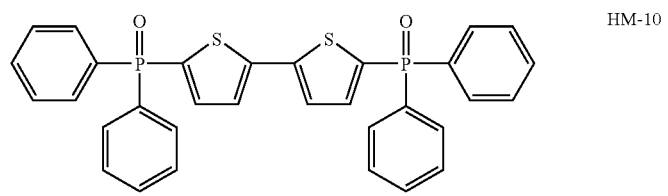
HM-10
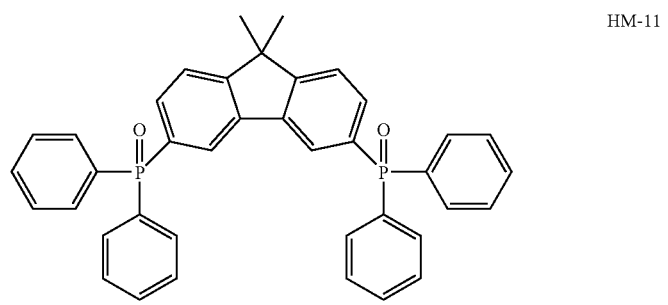
HM-11
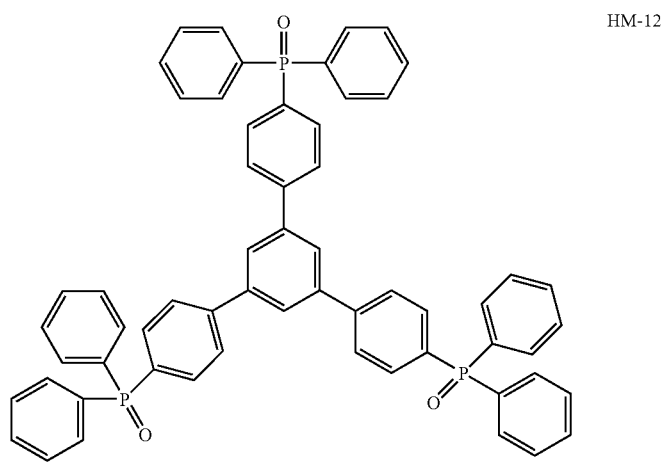
HM-12
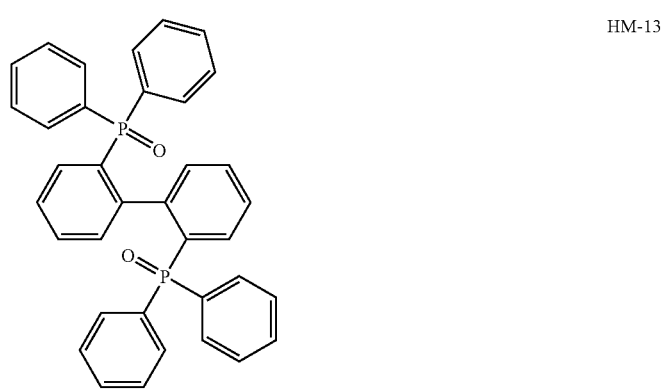
HM-13

-continued
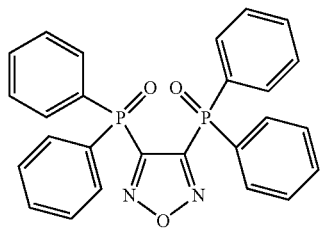
HM-14
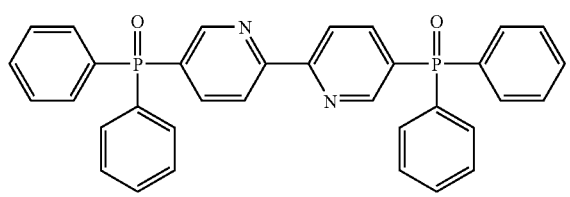
HM-15
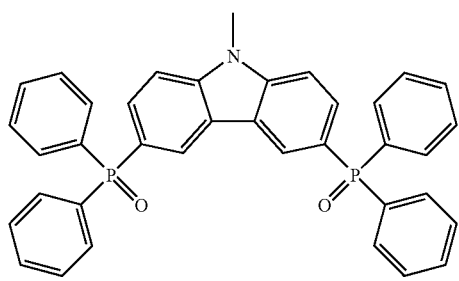
HM-16
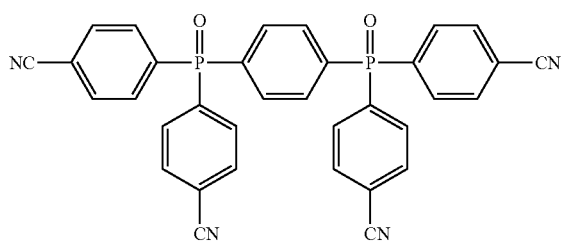
HM-17
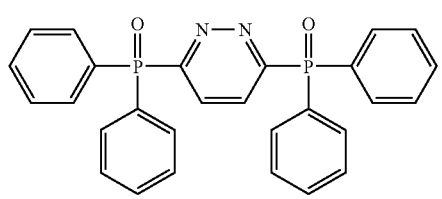
HM-18
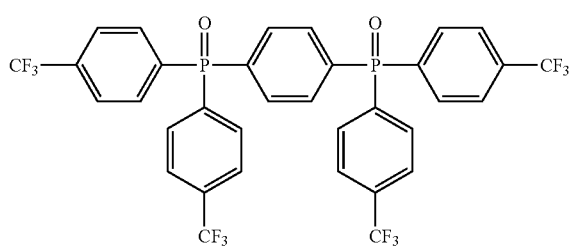
HM-19

-continued

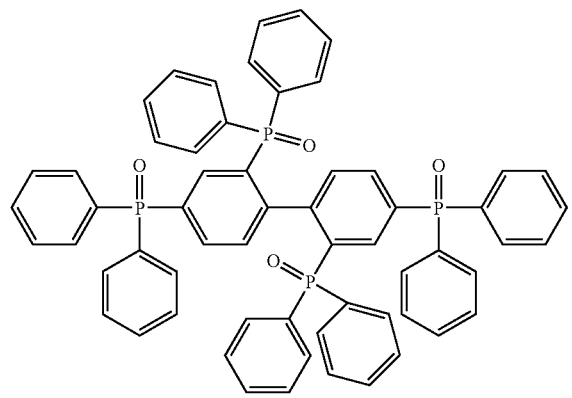
HM-20

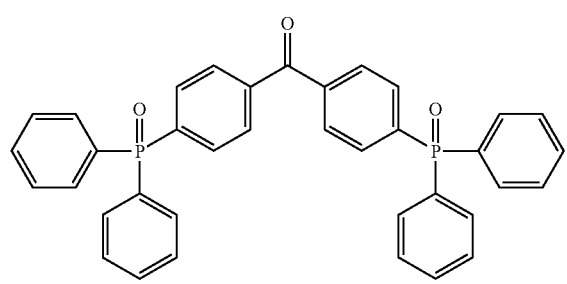
HM-21

The triplet state energy for a molecule is defined as the difference between the ground state energy (E(gs)) of the molecule and the energy of the lowest triplet state (E(ts)) of the molecule, both given in eV. These energies can be determined experimentally or calculated, for example, by using the B3LYP method as implemented in the Gaussian98 (Gaussian, Inc., Pittsburgh, Pa.) computer program. The basis set for use with the B3LYP method is defined as follows: MIDI! for all atoms for which MIDI! is defined, 6-31G* for all atoms defined in 6-31G* but not in MIDI!, and either the LACV3P or the LANL2DZ basis set and pseudopotential for atoms not defined in MIDI! or 6-31G*, with LACV3P being the preferred method. For any remaining atoms, any published basis set and pseudopotential may be used. MIDI!, 6-31G* and LANL2DZ are used as implemented in the Gaussian98 computer code and LACV3P is used as implemented in the Jaguar 4.1 (Schrodinger, Inc., Portland Oreg.) computer code. The energy of each state is computed at the minimum-energy geometry for that state. The difference in energy between the two states is further modified by Equation 1 to give the triplet state energy (Et):

$$Et=0.84*(E(ts)-E(gs))+0.35$$

For polymeric or oligomeric materials, it is sufficient to compute the triplet energy over a monomer or oligomer of sufficient size so that additional units do not substantially change the computed triplet energy.

General Device Architecture

The present invention can be employed in many OLED device configurations using small molecule materials, oligomeric materials, polymeric materials, or combinations thereof. These include very simple structures comprising a single anode and cathode to more complex devices, such as passive matrix displays comprised of orthogonal arrays of anodes and cathodes to form pixels, and active-matrix displays where each pixel is controlled independently, for example, with thin film transistors (TFTs).

There are numerous configurations of the organic layers wherein the present invention can be successfully practiced. The essential requirements of an OLED are an anode, a cathode, and an organic light emitting layer located between the anode and cathode. Additional layers may be employed as more fully described hereafter.

A typical structure according to the present invention and especially useful for a small molecule device, is shown in the FIGURE and is comprised of a substrate 101, an anode 103, a hole injecting layer 105, a hole transporting layer 107, an exciton or electron blocking layer 108, a light emitting layer 109, a hole blocking layer 110, an electron transporting layer 111, and a cathode 113. These layers are described in detail below. Note that the substrate may alternatively be located adjacent to the cathode, or the substrate may actually constitute the anode or cathode. The organic layers between the anode and cathode are conveniently referred to as the organic EL element. Also, the total combined thickness of the organic layers is desirably less than 500 nm.

The anode and cathode of the OLED are connected to a voltage/current source 150 through electrical conductors 160. The OLED is operated by applying a potential between the anode and cathode such that the anode is at a more positive potential than the cathode. Holes are injected into the organic EL element from the anode and electrons are injected into the organic EL element at the cathode. Enhanced device stability can sometimes be achieved when the OLED is operated in an AC mode where, for some time period in the AC cycle, the potential bias is reversed and no current flows. An example of an AC driven OLED is described in U.S. Pat. No. 5,552,678.

Substrate

The OLED device of this invention is typically provided over a supporting substrate 101 where either the cathode or anode can be in contact with the substrate. The electrode in contact with the substrate is conveniently referred to as the bottom electrode. Conventionally, the bottom electrode is the anode, but this invention is not limited to that configuration. The substrate can either be light transmissive or opaque, depending on the intended direction of light emission. The light transmissive property is desirable for viewing the EL emission through the substrate. Transparent glass or plastic is commonly employed in such cases. The substrate can be a complex structure comprising multiple layers of materials. This is typically the case for active matrix substrates wherein TFTs are provided below the OLED layers. It is still necessary that the substrate, at least in the emissive pixelated areas, be comprised of largely transparent materials such as glass or polymers. For applications where the EL emission is viewed through the top electrode, the transmissive characteristic of the bottom support is immaterial, and therefore the substrate can be light transmissive, light absorbing or light reflective. Substrates for use in this case include, but are not limited to: glass, plastic, semiconductor materials such as silicon, ceramics, and circuit board materials. Again, the substrate can be a complex structure comprising multiple layers of materials such as found in active matrix TFT designs. It is necessary to provide in these device configurations a light-transparent top electrode.

Anode

When the desired electroluminescent light emission (EL) is viewed through the anode, the anode 103 should be transparent or substantially transparent to the emission of interest. Common transparent anode materials used in this invention are indium-tin oxide (ITO), indium-zinc oxide (IZO) and tin oxide, but other metal oxides can work including, but not limited to, aluminum- or indium-doped zinc oxide, magnesium-indium oxide, and nickel-tungsten oxide. In addition to these oxides, metal nitrides, such as gallium nitride, and metal selenides, such as zinc selenide, and metal sulfides, such as zinc sulfide, can be used as the anode. For applications where EL emission is viewed only through the cathode, any conductive material can be used, transparent, opaque or reflective. Example conductors for this application include, but are not limited to, gold, iridium, molybdenum, palladium, and platinum. Typical anode materials, transmissive or otherwise, have a work function of 4.1 eV or greater. Desired anode materials are commonly deposited by any suitable means such as evaporation, sputtering, chemical vapor deposition, or electrochemical means. Anodes can be patterned using well-known photolithographic processes. Optionally, anodes may be polished prior to application of other layers to reduce surface roughness so as to minimize shorts or enhance reflectivity.

Hole-Injecting Layer (HIL)

A hole injecting layer 105 may be provided between anode and hole transporting layer. The hole injecting layer can serve to improve the film formation property of subsequent organic layers and to facilitate injection of holes into the hole transporting layer. Suitable materials for use in the hole injecting layer include, but are not limited to, porphyrinic compounds as described in U.S. Pat. No. 4,720,432, plasma-deposited fluorocarbon polymers as described in U.S. Pat. No. 6,208,075, and some aromatic amines, for example, MTDATA (4,4',4"-tris[(3-methylphenyl)phenylamino]triphenylamine). Alternative hole injecting materials reportedly useful in organic EL devices are described in EP 0 891 121 and EP 1 029 909.

The thickness of a hole injection layer containing a plasma-deposited fluorocarbon polymer can be in the range of 0.2 nm to 15 nm and suitably in the range of 0.3 to 1.5 nm.

Hole-Transporting Layer (HTL)

The hole-transporting layer 107 contains at least one hole-transporting compound such as an aromatic tertiary amine, where the latter is understood to be a compound containing at least one trivalent nitrogen atom that is bonded only to carbon atoms, at least one of which is a member of an aromatic ring. In one form the aromatic tertiary amine can be an arylamine, such as a monoarylamine, diarylamine, triarylamine, or a polymeric arylamine. Exemplary monomeric triarylamines are illustrated by Klupfel et al. U.S. Pat. No. 3,180,730. Other suitable triarylamines substituted with one or more vinyl radicals and/or comprising at least one active hydrogen containing group are disclosed by Brantley et al U.S. Pat. Nos. 3,567,450 and 3,658,520.

A more preferred class of aromatic tertiary amines are those which include at least two aromatic tertiary amine moieties as described in U.S. Pat. Nos. 4,720,432 and 5,061,569. The hole-transporting layer can be formed of a single or a mixture of aromatic tertiary amine compounds. Illustrative of useful aromatic tertiary amines are the following:

1,1-Bis(4-di-p-tolylaminophenyl)cyclohexane
1,1-Bis(4-di-p-tolylaminophenyl)-4-phenylcyclohexane
N,N,N',N'-tetraphenyl-4,4'''-diamino-1,1':4',1":4''',1'''-quaterphenyl
Bis(4-dimethylamino-2-methylphenyl)phenylmethane
1,4-bis[2-[4-[N,N-di(p-toly)amino]phenyl]vinyl]benzene (BDTAPVB)
N,N,N',N'-Tetra-p-tolyl-4,4'-diaminobiphenyl
N,N,N',N'-Tetraphenyl-4,4'-diaminobiphenyl
N,N,N',N'-tetra-1-naphthyl-4,4'-diaminobiphenyl
N,N,N',N'-tetra-2-naphthyl-4,4'-diaminobiphenyl
N-Phenylcarbazole
4,4'-Bis[N-(1-naphthyl)-N-phenylamino]biphenyl (NPB)
4,4'-Bis[N-(1-naphthyl)-N-(2-naphthyl)amino]biphenyl (TNB)
4,4'-Bis[N-(1-naphthyl)-N-phenylamino]p-terphenyl
4,4'-Bis[N-(2-naphthyl)-N-phenylamino]biphenyl
4,4'-Bis[N-(3-acenaphthenyl)-N-phenylamino]biphenyl
1,5-Bis[N-(1-naphthyl)-N-phenylamino]naphthalene
4,4'-Bis[N-(9-anthryl)-N-phenylamino]biphenyl
4,4'-Bis[N-(1-anthryl)-N-phenylamino]-p-terphenyl
4,4'-Bis[N-(2-phenanthryl)-N-phenylamino]biphenyl
4,4'-Bis[N-(8-fluoranthenyl)-N-phenylamino]biphenyl
4,4'-Bis[N-(2-pyrenyl)-N-phenylamino]biphenyl
4,4'-Bis[N-(2-naphthacenyl)-N-phenylamino]biphenyl
4,4'-Bis[N-(2-perylenyl)-N-phenylamino]biphenyl
4,4'-Bis[N-(1-coronenyl)-N-phenylamino]biphenyl
2,6-Bis(di-p-tolylamino)naphthalene
2,6-Bis[di-(1-naphthyl)amino]naphthalene
2,6-Bis[N-(1-naphthyl)-N-(2-naphthyl)amino]naphthalene
N,N,N',N'-Tetra(2-naphthyl)-4,4"-diamino-p-terphenyl
4,4'-Bis {N-phenyl-N-[4-(1-naphthyl)-phenyl]amino}biphenyl
2,6-Bis[N,N-di(2-naphthyl)amino]fluorene
4,4',4"-tris[(3-methylphenyl)phenylamino]triphenylamine (MTDATA)
4,4'-Bis[N-(3-methylphenyl)-N-phenylamino]biphenyl (TPD)

Another class of useful hole-transporting materials includes polycyclic aromatic compounds as described in EP 1 009 041. Some hole-injecting materials described in EP 0 891 121 A1 and EP 1 029 909 A1, can also make useful hole-transporting materials. In addition, polymeric hole-transporting materials can be used including poly(N-vinylcarbazole) (PVK), polythiophenes, polypyrrole, polyaniline, and copolymers including poly(3,4-ethylenedioxythiophene)/poly(4-styrenesulfonate) also called PEDOT/PSS.

Light-Emitting Layer (LEL)

Suitably, the light-emitting layer of the OLED device comprises a host material and one or more guest materials for emitting light. At least one of the guest materials is suitably a fluorescent or phosphorescent material. The light-emitting guest material(s) is usually present in an amount less than the amount of host materials and is typically present in an amount of up to 15 wt % of the host, more typically from 0.1-10 wt % of the host. For convenience, the light-emitting guest material may be referred to as a light emitting dopant. A phosphorescent guest material may be referred to herein as a phosphorescent material, or phosphorescent dopant. The phosphorescent material is preferably a low molecular weight compound, but it may also be an oligomer or a polymer. It may be provided as a discrete material dispersed in the host material, or it may be bonded in some way to the host material, for example, covalently bonded into a polymeric host.

Host Materials for Phosphorescent Materials

Suitable host materials should be selected so that the triplet exciton can be transferred efficiently from the host material to the phosphorescent material. For this transfer to occur, it is a highly desirable condition that the excited state energy of the phosphorescent material be lower than the difference in energy between the lowest triplet state and the ground state of the host. However, the band gap of the host should not be chosen so large as to cause an unacceptable increase in the drive voltage of the OLED. Suitable host materials are described in WO 00/70655; WO 01/39234; WO 01/93642; WO 02/074015; WO 02/15645, and US 20020117662. Suitable hosts include certain aryl amines, triazoles, indoles and carbazole compounds. Examples of desirable hosts are 4,4'-N,N'-dicarbazole-biphenyl (CBP), 2,2'-dimethyl-4,4'-N,N'-dicarbazole-biphenyl, m-(N,N'-dicarbazole)benzene, and poly(N-vinylcarbazole), including their derivatives.

Desirable host materials are capable of forming a continuous film. The light-emitting layer may contain more than one host material in order to improve the device's film morphology, electrical properties, light emission efficiency, and lifetime. The light emitting layer may contain a first host material that has good hole-transporting properties, and a second host material that has good electron-transporting properties.

Phosphorescent Materials

Phosphorescent materials may be used singly or in combination with other phosphorescent materials, either in the same or different layers. Some other phosphorescent materials are described in WO 00/57676, WO 00/70655, WO 01/41512, WO 02/15645, US 2003/0017361, WO 01/93642, WO 01/39234, U.S. Pat. No. 6,458,475, WO 02/071813, U.S. Pat. No. 6,573,651, US 2002/0197511, WO 02/074015, U.S. Pat. No. 6,451,455, US 2003/0072964, US 2003/0068528, U.S. Pat. No. 6,413,656, U.S. Pat. No. 6,515,298, U.S. Pat. No. 6,451,415, U.S. Pat. No. 6,097,147, US 2003/0124381, US 2003/0059646, US 2003/0054198, EP 1 239 526, EP 1 238 981, EP 1 244 155, US 2002/0100906, US 2003/0068526, US 2003/0068535, JP 2003073387, JP 2003073388, US 2003/0141809, US 2003/0040627, JP 2003059667, JP 2003073665, and US 2002/0121638.

The emission wavelengths of cyclometallated Ir(III) complexes of the type $IrL_3$ and $IrL_2L'$, such as the green-emitting fac-tris(2-phenylpyridinato-N,$C^{2'}$)Iridium(III) and bis(2-phenylpyridinato-N,$C^{2'}$)Iridium(III)(acetylacetonate) may be shifted by substitution of electron donating or withdrawing groups at appropriate positions on the cyclometallating ligand L, or by choice of different heterocycles for the cyclometallating ligand L. The emission wavelengths may also be shifted by choice of the ancillary ligand L'. Examples of red emitters are the bis(2-(2'-benzothienyl)pyridinato-N,$C^{3'}$)Iridium(III)(acetylacetonate) and tris(2-phenylisoquinolinato-N,$C^{2'}$)Iridium(III). A blue-emitting example is bis(2-(4,6-diflourophenyl)-pyridinato-N,$C^{2'}$)Iridium(III)(picolinate).

Other important phosphorescent materials include cyclometallated Pt(II) complexes such as cis-bis(2-phenylpyridinato-N,$C^{2'}$)platinum(II), cis-bis(2-(2'-thienyl)pyridinato-N,$C^{3'}$) platinum(II), cis-bis(2-(2'-thienyl)quinolinato-N,$C^{5'}$) platinum(II), or (2-(4,6-diflourophenyl)pyridinato-NC2') platinum (II) acetylacetonate. Pt(II) porphyrin complexes such as 2,3,7,8,12,13,17,18-octaethyl-21H, 23H-porphine platinum(II) are also useful phosphorescent materials.

Still other examples of useful phosphorescent materials include coordination complexes of the trivalent lanthanides such as $Tb^{3+}$ and $Eu^{3+}$ (J. Kido et al, *Appl. Phys. Lett.*, 65, 2124 (1994))

The following are examples of suitable phosphorescent emissive materials:

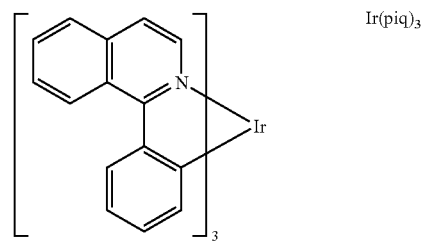

Ir(piq)$_3$

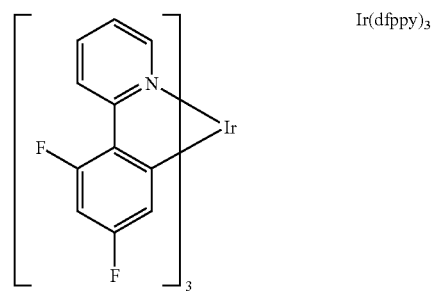

Ir(dfppy)$_3$

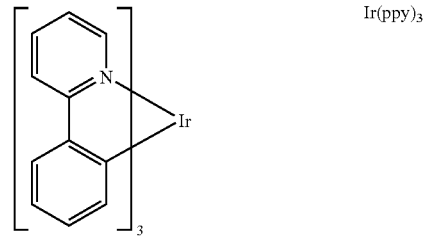

Ir(ppy)$_3$

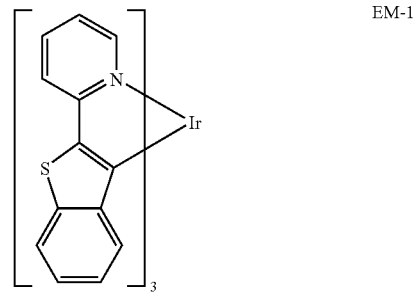

EM-1

-continued

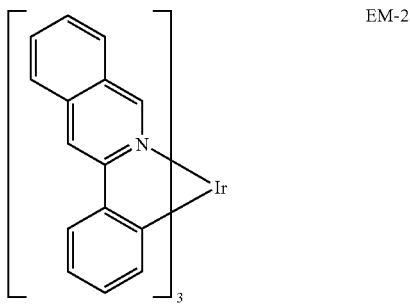

EM-2

Blocking Layers

In addition to suitable hosts, an OLED device employing a phosphorescent material often requires at least one exciton, electron, or hole blocking layer to help confine the excitons, electrons, or electron-hole recombination centers to the light-emitting layer comprising the host and phosphorescent material. In one embodiment, such a blocking layer would be placed between the electron-transporting layer and the light-emitting layer—see the FIGURE, layer 110. In this case, the ionization potential of the blocking layer should be such that there is an energy barrier for hole migration from the host into the electron-transporting layer, while the electron affinity should be such that electrons pass more readily from the electron-transporting layer into the light-emitting layer comprising host and phosphorescent material. It is further desired, but not absolutely required, that the triplet energy of the blocking material be greater than that of the phosphorescent material. Suitable hole-blocking materials are described in US 20020015859, WO 00/70655, WO 01/93642, US 20030068528 and US 20030175553. Two examples of useful materials are bathocuproine (BCP) and bis(2-methyl-8-quinolinolato)(4-phenylphenolato)Aluminum(III) (BAlQ). Metal complexes other than BAlQ are also known to block holes and excitons as described in US 20030068528. US 20030175553 describes the use of fac-tris(1-phenylpyrazolato-N,C 2)iridium(III) (Irppz) in an electron/exciton blocking layer.

Electron-Transporting Layer (ETL)

Preferred thin film-forming materials for use in forming the electron-transporting layer of the organic EL elements of this invention are metal chelated oxinoid compounds, including chelates of oxine itself (also commonly referred to as 8-quinolinol or 8-hydroxyquinoline). Such compounds help to inject and transport electrons, exhibit high levels of performance, and are readily fabricated in the form of thin films.

Other electron-transporting materials include various butadiene derivatives as disclosed in U.S. Pat. No. 4,356,429 and various heterocyclic optical brighteners as described in U.S. Pat. No. 4,539,507. Benzazoles and triazines are also useful electron-transporting materials.

Cathode

When light emission is viewed solely through the anode, the cathode used in this invention can be comprised of nearly any conductive material. Desirable materials have good film-forming properties to ensure good contact with the underlying organic layer, promote electron injection at low voltage, and have good stability. Useful cathode materials often contain a low work function metal (<4.0 eV) or metal alloy. One useful cathode material is comprised of a Mg:Ag alloy wherein the percentage of silver is in the range of 1 to 20%, as described in U.S. Pat. No. 4,885,221. Another suitable class of cathode materials includes bilayers comprising a thin electron-injection layer (EIL) in contact with an organic layer (e.g., an electron transporting layer (ETL)) which is capped with a thicker layer of a conductive metal. Here, the EIL preferably includes a low work function metal or metal salt, and if so, the thicker capping layer does not need to have a low work function. One such cathode is comprised of a thin layer of LiF followed by a thicker layer of Al as described in U.S. Pat. No. 5,677,572. An ETL material doped with an alkali metal, for example, Li-doped Alq, as disclosed in U.S. Pat. No. 6,013,384, is another example of a useful EIL. Other useful cathode material sets include, but are not limited to, those disclosed in U.S. Pat. Nos. 5,059,861, 5,059,862, and 6,140,763.

When light emission is viewed through the cathode, the cathode must be transparent or nearly transparent. For such applications, metals must be thin or one must use transparent conductive oxides, or a combination of these materials. Optically transparent cathodes have been described in more detail in U.S. Pat. Nos. 4,885,211, 5,247,190, JP 3,234,963, U.S. Pat. Nos. 5,703,436, 5,608,287, 5,837,391, 5,677,572, 5,776, 622, 5,776,623, 5,714,838, 5,969,474, 5,739,545, 5,981,306, 6,137,223, 6,140,763, 6,172,459, EP 1 076 368, U.S. Pat. Nos. 6,278,236, and 6,284,393. Cathode materials are typically deposited by any suitable methods such as evaporation, sputtering, or chemical vapor deposition. When needed, patterning can be achieved through many well known methods including, but not limited to, through-mask deposition, integral shadow masking as described in U.S. Pat. No. 5,276,380 and EP 0 732 868, laser ablation, and selective chemical vapor deposition.

Other Common Organic Layers and Device Architecture

In some instances, layers 109 and 111 can optionally be collapsed into a single layer that serves the function of supporting both light emission and electron transportation. Layers 110 and 111 may also be collapsed into a single layer that functions to block holes or excitons, and supports electron transportation. It also known in the art that emitting dopants may be included in the hole-transporting layer, which may serve as a host. Multiple dopants may be added to one or more layers in order to create a white-emitting OLED, for example, by combining blue- and yellow-emitting materials, cyan- and red-emitting materials, or red-, green-, and blue-emitting materials. White-emitting devices are described, for example, in EP 1 187 235, EP 1 182 244, U.S. Pat. Nos. 5,683,823, 5,503,910, 5,405,709, and 5,283,182, US 20020186214, US 20020025419, US 20040009367, and U.S. Pat. No. 6,627, 333.

This invention may be used in so-called stacked device architecture, for example, as taught in U.S. Pat. Nos. 5,703, 436 and 6,337,492.

Deposition of Organic Layers

The organic materials mentioned above are suitably deposited through a vapor-phase method such as sublimation, but can be deposited from a fluid, for example, from a solvent with an optional binder to improve film formation. If the material is a polymer, solvent deposition is useful but other methods can be used, such as sputtering or thermal transfer from a donor sheet. The material to be deposited by sublimation can be vaporized from a sublimation "boat" often comprised of a tantalum material, e.g., as described in U.S. Pat. No. 6,237,529, or can be first coated onto a donor sheet and then sublimed in closer proximity to the substrate. Layers with a mixture of materials can utilize separate sublimation boats or the materials can be pre-mixed and coated from a single boat or donor sheet. Patterned deposition can be achieved using shadow masks, integral shadow masks (U.S. Pat. No. 5,294,870), spatially-defined thermal dye transfer from a donor sheet (U.S. Pat. Nos. 5,688,551, 5,851,709 and 6,066,357) and inkjet method (U.S. Pat. No. 6,066,357).

Encapsulation

Most OLED devices are sensitive to moisture or oxygen, or both, so they are commonly sealed in an inert atmosphere such as nitrogen or argon. In sealing an OLED device in an inert environment, a protective cover can be attached using an organic adhesive, a metal solder, or a low melting temperature glass. Commonly, a getter or desiccant is also provided within the sealed space. Useful getters and desiccants include, alkali and alkaline metals, alumina, bauxite, calcium sulfate, clays, silica gel, zeolites, alkaline metal oxides, alkaline earth metal oxides, sulfates, or metal halides and perchlorates. Methods for encapsulation and desiccation include, but are not limited to, those described in U.S. Pat. No. 6,226,890. In addition, barrier layers such as SiOx, Teflon, and alternating inorganic/polymeric layers are known in the art for encapsulation.

Optical Optimization

OLED devices of this invention can employ various well-known optical effects in order to enhance its properties if desired. This includes optimizing layer thicknesses to yield maximum light transmission, providing dielectric mirror structures, replacing reflective electrodes with light-absorbing electrodes, providing anti glare or anti-reflection coatings over the display, providing a polarizing medium over the display, or providing colored, neutral density, or color conversion filters in functional relationship with the light emitting areas of the display. Filters, polarizers, and anti-glare or anti-reflection coatings can also be provided over a cover or as part of a cover.

The OLED device may have a microcavity structure. In one useful example, one of the metallic electrodes is essentially opaque and reflective; the other one is reflective and semi-transparent. The reflective electrode is preferably selected from Au, Ag, Mg, Ca, or alloys thereof. Because of the presence of the two reflecting metal electrodes, the device has a microcavity structure. The strong optical interference in this structure results in a resonance condition. Emission near the resonance wavelength is enhanced and emission away from the resonance wavelength is depressed. The optical path length can be tuned by selecting the thickness of the organic layers or by placing a transparent optical spacer between the electrodes. For example, an OLED device of this invention can have ITO spacer layer placed between a reflective anode and the organic EL media, with a semitransparent cathode over the organic EL media.

EXAMPLES

The invention has been described in detail with particular reference to certain preferred embodiments thereof, but it will be understood that variations and modifications can be effected within the spirit and scope of the invention.

Synthesis Example 1

Synthesis of Compound HM-1

Sodium hydride (12 mmol, in the form of a 60 wt % suspension in mineral) oil was added to a stirred solution of diphenylphosphineoxide (12 mmol) in dry N,N'-dimethylformamide (22 ml) at room temperature under nitrogen. With evolution of hydrogen a yellow solution was formed. Then, p-difluorobenzene (6 mmol) was added and the mixture was warmed to 140° C. The yellow color gradually faded and after 9 hours the product mixture was cooled and acidified with dilute hydrochloride acid. The product was extracted with chloroform, washed with sodium hydrogen carbonate and dried over magnesium sulfate. On evaporation of all chloroform the crude and almost pure product was obtained as colorless oil (90%) which after recrystallization with a dichloromethane/dimethylether mixture gave pure 1,4-phenylbis-diphenylphosphineoxide (HM-1).

Synthesis Example 2

Synthesis of Compound HM-2

Sodium hydride (12 mmol, in the form of a 60 wt % suspension in mineral) oil was added to a stirred solution of diphenylphosphineoxide (12 mmol) in dry N,N'-dimethylformamide (22 ml) at room temperature under nitrogen. With evolution of hydrogen a yellow solution was formed. Then, 4,4'-difluorobiphenyl (6 mmol) was added and the mixture was warmed to 140° C. The yellow color gradually faded and after 24 hours the product mixture was cooled and acidified with dilute hydrochloride acid. The product was extracted with chloroform, washed with sodium hydrogen carbonate and dried over magnesium sulfate. On evaporation of all chloroform the crude and almost pure product was obtained as colorless oil (84%) which after recrystallization with a dichloromethane/dimethylether mixture gave pure 4,4'-biphenylbis-diphenylphosphineoxide (HM-2).

Synthesis Example 3

Synthesis of Compound HM-3

Sodium hydride (12 mmol, in the form of a 60 wt % suspension in mineral) oil was added to a stirred solution of diphenylphosphineoxide (12 mmol) in dry N,N'-dimethylformamide (22 ml) at room temperature under nitrogen. With evolution of hydrogen a yellow solution was formed. Then, 2,6-difluoropyridine (6 mmol) was added and the mixture was stirred at room temperature. The yellow color gradually faded and after overnight the product mixture was cooled and acidified with dilute hydrochloride acid. The product was extracted with chloroform, washed with sodium hydrogen carbonate and dried over magnesium sulfate. On evaporation of all chloroform the crude and almost pure product was obtained as colorless oil (95%) which after recrystallization with a dichloromethane/dimethylether mixture gave pure 2,6-pyridylbis-diphenylphosphineoxide (HM-3).

Calculation Example

The calculated T1 values of compounds HM-1, HM-2 and HM-3 are listed in Table 1. From Table 1, it is seen that HM-1, HM-2 and HM-3 all have high triplet energies, which makes them suitable host materials for red, green and blue phosphorescent devices.

TABLE 1

| Compound | Eg(T1), eV |
|---|---|
| HM-1 | 3.4 |
| HM-2 | 2.9 |
| HM-3 | 3.1 |

Device Example 4

4,4'-Bis[N-(1-naphthyl)-N-phenylamino]biphenyl (NPB) was vacuum deposited on a cleaned ITO substrate to a deposit thickness of 115 nm. The phosphineoxide compound HM-1 and Ir(piq)$_3$ were vacuum co-deposited on the NPB layer at a weight ratio of 12.5:1 to a thickness of 35 nm. The phosphineoxide compound (functions as hole/exciton blocking layer) was vacuum deposited on the light-emitting layer at a thickness of 10 nm. A 40 nm layer of aluminum tris(8-hydroxyquinoline) (Alq) was vacuum deposited on the top of the neat phosphineoxide layer. A pattern mask (0.1 cm$^2$) was put on the thus formed organic thin film, and lithium fluoride was vacuum deposited to a thickness of 1 nm, and aluminum was then vacuum deposited to a thickness of 100 nm to complete an OLED.

The device was encapsulated in a dry box. On applying a DC voltage to the resulting OLED by use of Source-Measure Unit Model 2400, red light emission was obtained. The red luminescence had CIE chromaticity coordinate of (x, y)= (0.65, 0.34) as measured with Spectral Analyzer. The voltage and luminance properties of the devices at a constant current density of 20 mA/cm$^2$ are shown in Table 2.

Device Example 5

An OLED was prepared in the same manner as in Example 4, except for replacing HM-1 with HM-2. The resulting OLED was evaluated in the same manner as in Example 1.

Device Example 6

An OLED was prepared in the same manner as in Example 4, except for replacing HM-1 with HM-3. The resulting OLED was evaluated in the same manner as in Example 1.

Example 7

Comparative

An OLED was prepared in the same manner as in Example 4, except for replacing HM-1 with BAlq shown below. The resulting OLED was evaluated in the same manner as in Example 1. Red light emission was obtained. The voltage and luminance properties of the devices 4-7 at a constant current density of 20 mA/cm$^2$ are also shown in Table 2.

TABLE 2

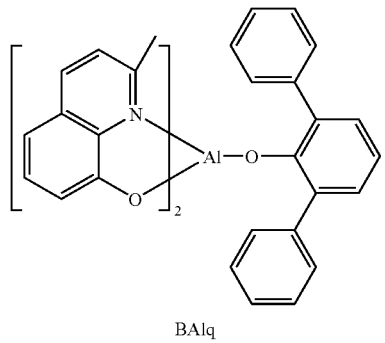

BAlq

| Device Example | Type | Drive Voltage, V | Yield, Cd/A |
|---|---|---|---|
| 4 | Inventive | 10.7 | 3.93 |
| 5 | Inventive | 9.78 | 3.41 |
| 6 | Inventive | 12.3 | 7.53 |
| 7 | Comparison | 12.3 | 4.24 |

From the data presented in Table 2, it is seen that a red phosphorescent OLED comprising Bis-phosphineoxide compounds as both a host material and an exciton/hole blocking material exhibits much lower driving voltage in general when compared to an OLED comprising the conventional host material BAlq (Ex 7). The luminescence efficiencies of devices 4 and 5 are very close to that of the BAlq device, where the luminescence efficiency of device 6 is much higher than that of the BAlq device.

Device Example 8

4,4'-Bis[N-(1-naphthyl)-N-phenylamino]biphenyl (NPB) was vacuum deposited on a cleaned ITO substrate to a deposit thickness of 75 nm. The phosphineoxide compound HM-2 and Ir(ppy)$_3$ were vacuum co-deposited on the NPB layer at a weight ratio of 12.5:1 to a thickness of 35 nm, and the phosphineoxide compound (functions as hole/exciton blocking layer) was deposited thereon to a thickness of 10 nm. A 40 nm layer of aluminum tris(8-hydroxyquinoline) (Alq) was vacuum deposited on the top of the neat phosphineoxide layer. A pattern mask (0.1 cm$^2$) was put on the thus formed organic thin film, and lithium fluoride was vacuum deposited to a thickness of 1 nm, and aluminum was then vacuum deposited to a thickness of 100 nm to complete an OLED.

Device 8 was encapsulated in a dry box. On applying a DC voltage to the resulting OLED by use of Source-Measure Unit Model 2400, green light emission was obtained. The green luminescence had CIE chromaticity coordinate of (x, y)= (0.28, 0.63) as measured with Spectral Analyzer. The voltage and luminance properties of the device at a constant current density of 20 mA/cm$^2$ are shown in Table 3.

Example 9

Comparative

An OLED was prepared in the same manner as in Example 8, except for replacing compound HM-2 with tri(naphthyl) phosphine oxide (C-2) shown below. The resulting OLED was evaluated in the same manner as in Example 8. Green light emission was obtained. The voltage and luminance properties of the devices at a constant current density of 20 mA/cm$^2$ are also shown in Table 3.

TABLE 3

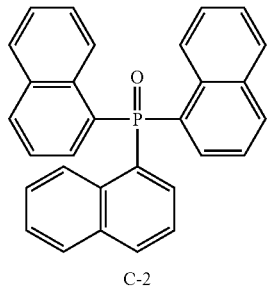

C-2

| Device Example | Type | Drive Voltage, V | Yield, Cd/A |
|---|---|---|---|
| 8 | Inventive | 9.23 | 11.5 |
| 9 | Comparison | 10.4 | 1.25 |

From the data presented in Table 3, it is seen that compound C-2 (a compound disclosed in JP-A-2004204140) is not a suitable host material for green phosphorescent OLEDs. The triplet energy of tri(naphthyl)phosphine oxide is calculated to be 2.6 eV, which is slightly higher than the triplet energy of the green dopant (2.5 eV). Such a small energy difference may not be able to ensure complete energy transfer from host to dopant. Moreover, C-2 is a very crystalline material. Its high tendency to crystallize may cause some interlayer contact problems in the device, resulting in the observed low device efficiency. Further, it is worthy to note that the triplet energies of C-2 and its derivatives are too low for blue phosphorescent devices.

PARTS LIST

101 Substrate
103 Anode
105 Hole-Injecting layer (HIL)
107 Hole-Transporting layer (HTL)
108 Exciton or electron blocking layer (EBL)
109 Light-Emitting layer (LEL)
110 Hole and/or exciton blocking layer
111 Electron-Transporting layer (ETL)
113 Cathode
150 Current/Voltage source
160 Electrical conductors

The invention claimed is:

1. An OLED device comprising an anode and a cathode and having therebetween a light emitting layer containing a host and an emissive material, wherein the host material is a phosphineoxide compound bearing two or more tri(hetero)arylphosphineoxide groups, provided these groups are selected to give a compound with a Et≧2.65 eV.

2. The device of claim 1 that emits light in the green or blue region of the visible spectrum, or together with the emission of another layer, emits white light.

3. The device of claim 1 wherein the device contains an exciton or hole blocking layer located between the cathode and the light emitting layer that contains a phosphineoxide compound bearing two or more tri(hetero)arylphosphineoxide groups, provided these groups are selected to give a compound with a Et≧2.65 eV.

4. The device of claim 3 that emits light in the green or blue region of the visible spectrum, or together with the emission of another layer, emits white light.

5. The device of claim 1 wherein the device contains an electron-transporting layer located between the cathode and the anode and contains a phosphineoxide compound bearing two or more tri(hetero)arylphosphineoxide groups provided the tri(hetero)arylphosphineoxide groups selected to give a compound with a Et≧2.65 eV.

6. The device of claim 1 wherein the phosphineoxide compound is represented by the formula:

(A)$_n$B wherein each A is independently represented by:

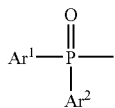

and
n≧2;
wherein Ar$^1$, Ar$^2$ and B each represent groups selected to give a compound with a Et≧2.65 eV and;
Ar$^1$, Ar$^2$ and B are each an aromatic group or heteroaromatic group independently selected from phenyl, biphenyl, and heteroaryl groups which may be independently substituted with one or more of alkyl, alkenyl, alkoxy, aryl, aralkyl, halogen, NH$_2$, NHR, NR$_2$, NO$_2$ and CN groups;
provided that one or more of Ar$^1$, Ar$^2$ and B may be linked together by a linking group selected from a covalent bond, —O—, —CH$_2$—, —CHR—, —CR$_2$—, —NH—, and —NR— in which each R is selected from alkyl, alkenyl, aryl, and aralkyl groups; and
B is a (hetero)aromatic group with n bonds.

7. The device of claim 6 wherein the phosphineoxide compound is represented by the formula:

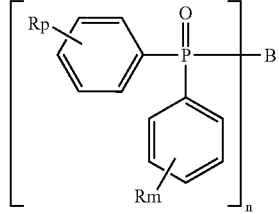

wherein
B comprises an aromatic group or heteroaromatic group independently selected from phenyl, biphenyl, and heteroaryl with Et≧2.65 eV;
each R is independently selected from alkyl, alkenyl, alkoxy, aryl, aralkyl, halogen, NH$_2$, NHR, NR$_2$, NO$_2$ and CN groups;
each of p and m is independently selected from the values 0, 1, 2, 3 and 4; and
n is at least 2.

8. The device of claim 6 wherein B is a chain of 2 or more aromatic ring groups.

9. The device of claim 1 wherein the light emitting layer contains at least two host materials.

10. The device of claim 1 wherein the emissive material is a phosphorescent dye.

11. The device of claim 1 wherein the emissive material is a blue or green phosphorescent dye.

12. The device of claim 1 wherein the light emitted by the device is white.

13. The device of claim 1 wherein Et≧2.8 eV.

* * * * *